(12) United States Patent
Spencer

(10) Patent No.: US 6,348,049 B1
(45) Date of Patent: *Feb. 19, 2002

(54) SURGICAL/MEDICAL TUBING AND CONTAINERS FOR USE IN CONVEYING MEDICAL SOLUTIONS AND THE LIKE

(75) Inventor: Dudley W. C. Spencer, Wilmington, DE (US)

(73) Assignee: Denco, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/803,779

(22) Filed: Feb. 24, 1997

Related U.S. Application Data

(60) Continuation-in-part of application No. 08/742,046, filed on Nov. 1, 1996, now Pat. No. 5,733,268, and a continuation-in-part of application No. 08/443,196, filed on May 17, 1995, now abandoned, which is a division of application No. 08/219,828, filed on Mar. 30, 1994, now Pat. No. 5,496,291.

(51) Int. Cl.7 ............................................. A61M 25/00
(52) U.S. Cl. ........................ 604/523; 604/265; 604/93
(58) Field of Search .................. 604/93, 264, 280–283, 604/265, 523–539; 138/118; 525/173, 175, 176; 428/36.8, 36.9, 36.92, 480

(56) References Cited

U.S. PATENT DOCUMENTS

| | | | |
|---|---|---|---|
| 4,010,222 A | | 3/1977 | Shih |
| 4,048,254 A | * | 9/1977 | Hillier et al. |
| 4,219,628 A | | 8/1980 | Weemes et al. |
| 4,322,335 A | | 3/1982 | Nield |
| 4,337,947 A | | 7/1982 | Saito et al. |
| 4,344,874 A | | 8/1982 | Akagi et al. |
| 4,616,064 A | | 10/1986 | Zukosky et al. |
| 4,628,072 A | | 12/1986 | Shiraki et al. |
| 4,657,970 A | | 4/1987 | Shiraki et al. |
| 4,670,510 A | * | 6/1987 | Kobayashi et al. |
| 4,680,344 A | | 7/1987 | Coker |
| 4,778,842 A | | 10/1988 | Taniguchi et al. |
| 4,806,588 A | | 2/1989 | Fujimoto et al. |
| 4,816,343 A | * | 3/1989 | Muller et al. |
| 4,820,768 A | | 4/1989 | Shiraki et al. |
| 4,861,830 A | | 8/1989 | Ward, Jr. |
| 4,868,243 A | | 9/1989 | Gelles et al. |
| 4,906,687 A | | 3/1990 | Modic |
| 4,914,152 A | | 4/1990 | Miyashita et al. |
| 4,954,568 A | | 9/1990 | Gelles et al. |
| 4,968,464 A | | 11/1990 | Kojoh et al. |
| 5,089,553 A | | 2/1992 | Umeda et al. |
| 5,091,459 A | | 2/1992 | Howe |
| 5,112,915 A | | 5/1992 | Morelli et al. |
| 5,115,012 A | | 5/1992 | Howe |
| 5,453,099 A | | 9/1995 | Lee et al. |
| 5,496,291 A | * | 3/1996 | Spencer ...................... 604/280 |
| 5,733,268 A | * | 3/1998 | Spencer ...................... 604/264 |

OTHER PUBLICATIONS

Research Disclosure, May 1989, pp. 329–330, No. 301 XP 000052490 Blends of Polyester–Ethers with Ethylene–Acrylic Acid Copolymers.

* cited by examiner

Primary Examiner—Jeffrey R. Jastrzab

(57) ABSTRACT

Surgical/medical tubing and containers are made from an ionomeric modified poly-ether-ester plastic material is used as a substitute for the conventional uses of polyvinyl chloride. The ionomeric modified poly-ether-ester has various advantages which make it particularly suitable for such uses, as well as other uses such as other medical containers, for tubing in food processing and as sheets and films for bacterial and virus exclusion.

14 Claims, 4 Drawing Sheets

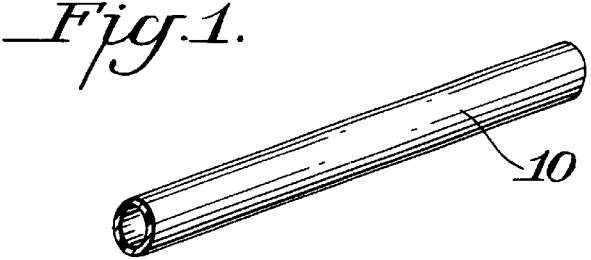
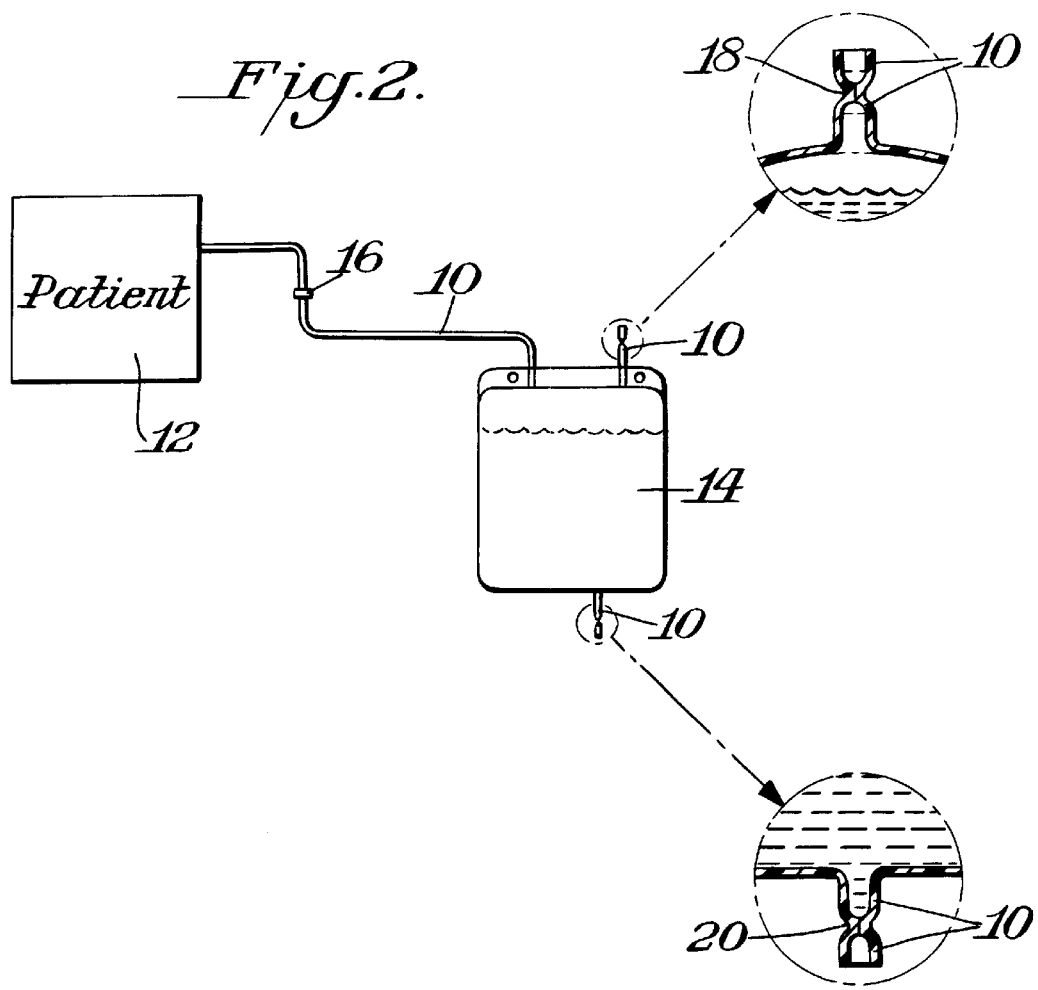

SURGICAL/MEDICAL TUBING AND CONTAINERS FOR USE IN CONVEYING MEDICAL SOLUTIONS AND THE LIKE

CROSS-REFERENCE TO RELATED APPLICATION

This application is a continuation-in-part of application Ser. No. 08/443,196, filed May 17, 1995 now abandoned which in turn is a division of application Ser. No. 08/219,828, filed Mar. 30, 1994, now U.S. Pat. No. 5,496,291; and is a continuation-in-part of Ser. No. 08/742,046, filed Nov. 1, 1996 now U.S. Pat. No. 5,733,268.

BACKGROUND OF THE INVENTION

Polyvinylchloride (PVC) is the accepted material for use as tubing in various medical applications, such as peritoneal dialysis, blood processing, chemotherapy and other uses. In such uses, a consumable is conveyed through the tubing from one location to another. For peritoneal dialysis (CAPD), for example, it is also the practice to replace a used dialysate bag with a new bag. This is accomplished by cutting through the PVC tubing leading from the used bag and then welding tubing from a new bag to the cut portion of the tubing so that one bag may replace another. PVC is also the generally accepted material for forming bags and other medical containers and is commonly used as tubing in food processing particularly for fluids and semi-solids. In addition, PVC is the material generally used for forming sheets and films for bacterial and virus exclusion. Despite its acceptance by the art, PVC has a number of disadvantages which would be desirable to overcome in such uses. For example, conventional PVC includes a plasticizer (DOP) which might leach into the solutions in the bag. Further, after PVC has leached its DOP, large volumes of PVC particulates are released. Other disadvantages will be later referred to.

U.S. Pat. No. 4,048,254 (Hillier) and U.S. Pat. No. 4,816,343 (Mueller) disclose materials intended to replace PVC. U.S. Pat. No. 4,670,510 (Kobayashi) discloses polyester block copolymer compositions having rubber-like elasticity. Such compositions includes polyester ethers.

SUMMARY OF THE INVENTION

An object of this invention is to provide a material which will act as an improved replacement for PVC in the conventional uses of PVC.

A further object of this invention is to provide such a material which can be used as tubing for medical applications, as bags and other medical containers, for tubing food processing and as sheets and films for bacterial and virus exclusion.

In accordance with this invention the material which meets the above objects is an ionomeric modified poly-ether-ester. The ionomeric modifier is added in a range of 1% to 20% depending upon the end use requirement.

THE DRAWINGS

FIG. 1 is a perspective view of a tube made from ionomeric modified poly-ether-ester in accordance with this invention;

FIG. 2 is a schematic view of a urinary drainage system utilizing the tubing of FIG. 1;

FIG. 2A is an enlarged cross-sectional view of a top air seal shown in the corresponding circled portion of FIG. 2;

FIG. 2B is an enlarged cross-sectional view of a discharge line in the corresponding circled portion of FIG. 2;

DETAILED DESCRIPTION

Figure 3:
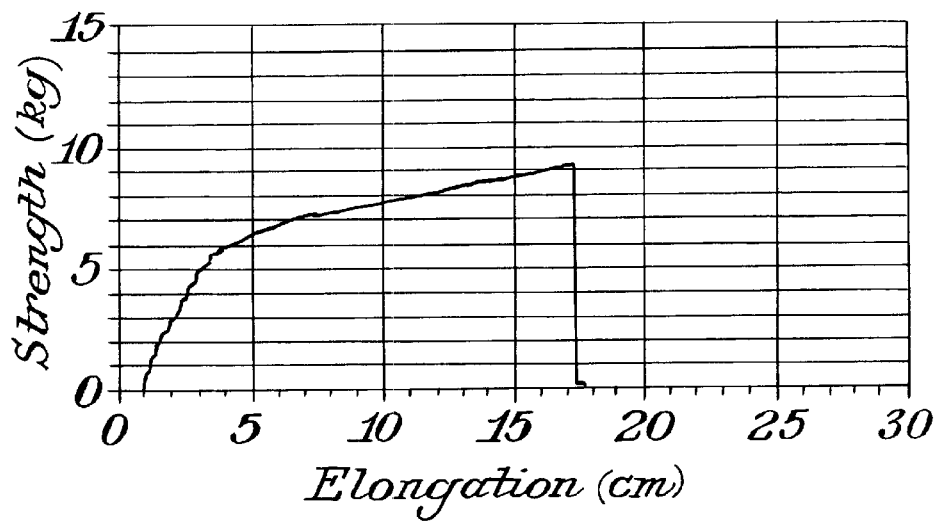
FIGS. 3–4 are graphs comparing the elongation and strength characteristics of PVC welded to the material of this invention (FIG. 3) and of the ionomeric modified poly-ether-ester of this invention alone (FIG. 4)

The present invention is directed to providing a material which can be used as a substitute for PVC in the conventional uses of PVC while having advantages over such PVC material. The material of this invention is an ionomeric modified poly-ether-ester. Poly-ether-ester is a well known material generally used to take advantage of its high strength characteristics. Such material is used, for example, in clothing generally referred to as polyester clothing. ordinarily, the strength of such material would make it unsuitable for use as a substitute for PVC in the uses of PVC with which this invention deals. It has been discovered, however, that the poly-ether-ester material can be modified by incorporation of a small amount of an ionomer which would modify the characteristics of the poly-ether-ester by giving it sufficient fragility to, for example, permit the material when used as a sealed tube to pop open. The specific amount of ionomer would depend upon the end use.

In general, the ionomeric modifier comprises from 0.5–50% by weight and preferably from 1% to 25% by weight of the combination depending upon the end use requirement. For example, in tubing such as for CAPD use where the material is to be sealed, welded and the lumen reopened the broad ionomer composition range would be 2% to 15%, a more preferred range of 3% –10% by weight. A range of 7–10% by weight is ideal. The result is a tube which is strong, sufficiently rubber like, and a degree of fracture to make reopening of the sealed tubes by finger pressure. For bags, films and other thin structures the ionomer would be present in a range of from 1% to 50% by weight of the combination depending on the end use requirements. For food processing tubes and aseptic surgical draping procedures a range of 10% to 20% by weight is desirable. For implanted catheters and sutures the range of 0.5 to 1% by weight is preferred.

The material of this invention is thus an ionomeric modified poly-ether-ester wherein the material has from 1% to 25% by weight ionomer and from 99% to 75% by weight poly-ether-ester with mixtures of 50–50% by weight being feasible. The basic material components are as follows:
Poly-ether-ester
POLY-ETHER-ESTER BLOCK COPOLYMER (Block poly-ether-ester) (Co-poly-ether-ester) (Polyester elastomer)

(Thermoplastic poly-ether-ester) Tradenames: Hytrel, Lomod, Pelprene. A block copolymer containing both polyether and ester blocks. The best known example is poly-(tetramethyleneterephthalate-b-poly-oxytetramethyleneterephthalate).

Ionomer

IONOMER Trade name Surlyn. A copolymer of ethylene with 1–10% by weight methacrylic acid, which has been converted to methacrylate salt, often the sodium, magnesium or zinc salt, by neutralization with the appropriate base. The resultant ionic groups tend to aggregate to form domains which act as physical crosslinks for the polyethylene. However, the domains break down on heating, so the material may be melt processed as other thermoplastics. The copolymers are produced by the high pressure ethylene polymerization process and so are similar to low density polyethylene. The comonomer decreases crystallinity but consequent loss of stiffness is restored by the physical crosslinks. The material is more transparent than LDPE and shows better adhesion, which makes it useful as a layer in laminated coextruded packaging films and in, therefore, homogenous mixing.

| Property | ASTM Test | Units | Typical | |
|---|---|---|---|---|
| Material Properties Poly-ether-ester | | | | |
| Hardness, Durometer D | D 2240 | points | | 30 |
| Hardness, Durometer A | D 2240 | points | | 85 |
| Processing | | | | |
| Melt Flow Rate at 190° C. (374° F.)/2.16 g load | D 1238 | g/10 min | | 5 |
| Melting Point | D 3418$^b$ | | | |
| Peak of Endotherm | | ° C.(F.) | 170 | (338) |
| Extrapolated End Point | | ° C.(° F.) | 200 | (392) |
| Stress/Strain | D 638$^c$ | | | |
| Tensile Strength | | MPa(psi) | 26.2 | (3800) |
| Elongation at Break | | % | | 700 |
| Stress at 5% Strain | | MPa(psi) | 1.3 | (190) |
| Stress at 10% Strain | | MPa(psi) | 2.1 | (300) |
| Stress at 15% Strain | | MPa(psi) | 2.6 | (390) |
| Stiffness | | | | |
| Flexural Modulus: | D 790$^d$ | | | |
| at −40° C.(−40° F.) | | MPa(psi) | 145 | (21,000) |
| at 23° C.(73° F.) | | MPa(psi) | 28 | (4,000) |
| at 100° C.(212° F.) | | MPa(psi) | 14 | (2,000) |
| Brittleness Temperature, Solenoid | D 746 | ° C.(° F.) | <−105 | (<−157) |
| Toughness | | | | |
| Initial Tear Resistance, Die C | D 1004$^e$ | kN/m (b f/n) | 77 | (440) |
| Resistance to Flex Cut Growth, Ross(pierced) | D 1052 | cycles to 5x cut growth | | >1 × 10$^6$ |
| Izod Impact (Notched) | D 256f | | | |
| at −40° C.(−40° F.) | | J/m(ft · b f/n) | | No Break |
| at 23° C.(73° F.) | | J/m(ft · b f/n) | | No Break |
| Abrasion Resistance | | | | |
| Tober, CS-17 wheel, 1 kg load | D 1044 | mg/1,000 cycles | | 2 |
| Tober, H-18 wheel, 1 kg load | D 1044 | mg/1,000 cycles | | 90 |
| Miscellaneous | | | | |
| Compression set, after 22 h at 70° C.(158° F.) 2.8 MPa (400 psi) load | D 395$^g$ | % | | 16 |
| Specific Gravity | D 792 | * | | 1.07 |
| Water Absorption (24 h) | D 570 | % | | 3 |
| Softening Point, Vicat | D 1525$^h$ | ° C.(° F.) | 83 | (181) |
| Heat Deflection Temperature | D 648 | | | |
| 0.5 MPa (66 psi) | | ° C.(° F.) | 46 | (115) |

| Film Property (2 mll blow, 3:1 BUR) | Typical Value | Test Method |
|---|---|---|
| Ultimate Tensile Strength, MD/TD, psi (MPa) | 4900 (33.8)/5900 (40.7) | ASTM D-882 |
| Ultimate Elongation, MD/TD, % | 350/400 | ASTM D-882 |
| Secant Modulus, MD/TD, psi (MPa) | 35000 (241)/38,000 (262) | ASTM D-882 |
| Spencer Impact Strength, in lb mil (J/mm) | 7.0 (31) | ASTM D-342C |
| Dart Drop Strength g. mil (g. μm) | 300 (11.8) | ASTM D-1709 Method B |
| Elmerdorf Tear Strength, MD/TD, g/mil (m μm) | 18 (6.9)/19 (7.3) | ASTM D-1922 |
| Gloss 20° | 75 | ASTM D-2457 |
| % Haze | 30 | ASTM D-1003 |

-continued

| Resin Property | Typical Value | Test Method |
| --- | --- | --- |
| Melt flow index, dg, min | 13 | ASTM D-1238 condition 190.2*6 |
| Melt Point, °C. (°F.) | 98 (208) | ASTM D-34*8 (DSC) |
| Freeze Point, °C. (°F.) | 68 (154) | ASTM D-34*8 (DSC) |
| Vicat softening point, °C. (°F.) | 74 (165) | ASTM D-1525 |
| Ion type | Sodium | — |

Poly-ether-esters are valuable materials because they have excellent low temperature properties (freezing) and are impervious to chemicals, oils and tissue. They have one serious negative, however, for many end-uses: They stretch 7× their length under low stress. For example, a tube one foot long will stretch to seven feet before breaking. Industrial goods such as bags, films, tubes, etc. readily warp out of shape and become unacceptable as end-use products. The present invention adds an ionomer to the composition to make useful, thin products.

Ionomers are somewhat like polyethylene in that they are useful as films because they are excellent for food wrapping, medical and pharmaceutical packing and are impervious to most oils and chemicals. Like polyethylene, they puncture readily and only stretch 3× before fracture.

A common use is a coating over stronger materials and are frequently used as a co-extrusions on nylon and other films to provide heat sealing.

The invention makes use of the fact that both poly-ester-ethers and ionomers melt at the same temperature. (191° C.) Instead of a coating, the invention mixes them together. In this way, the negatives of the two materials could be adjusted in a variety of ways to make new materials that are stronger than the ionomers, and less stretchy than the poly-ether-esters.

Combining the two materials as described also reduces another major limitation of the poly-ester-ethers (P.E.E.). They can absorb excessive moisture depending upon temperature and humidity. In the case of P.E.E. use in autoclaved (steam sterilized) medical tubing for example, the moisture pick-up makes the tubing unacceptable for further processing. Adding 5% to 7% by weight ionomer to the composition reduces the moisture absorbance to less than 1% by weight. A level comparable to medical grade PVC and well within the limits required for TCD® to welding.

For forming the material of this invention the following process may be used. The two materials are fed separately in pellet form into a single screw extruder. A twin screw extruder could be used satisfactorily but a single screw is sufficient and simpler to control. The two pellet streams are mixed to the required ratios and fed into the extruder. Extrusion rates of 10 to 250 lbs per hour are practical at melt temperatures of 180° C. to 200° C., with 191° C. being ideal. The melt is fed through a sizing die and liquid quenched as it exits the die for accuracy and handling purposes.

A typical extruder heating and mixing profile would involve feeding the ionomeric and P.E.E. pellets from individual feed hoppers into the extruder where the feed zone of the extruder is at 300° F. The material would then pass to a compression zone at 350° F. The materials would then pass into a melting zone at 375° F. Finally, the material would be extruded into the desired shapes. Techniques such as conventionally used for PVC could then be used for forming the end products.

Figure 4:
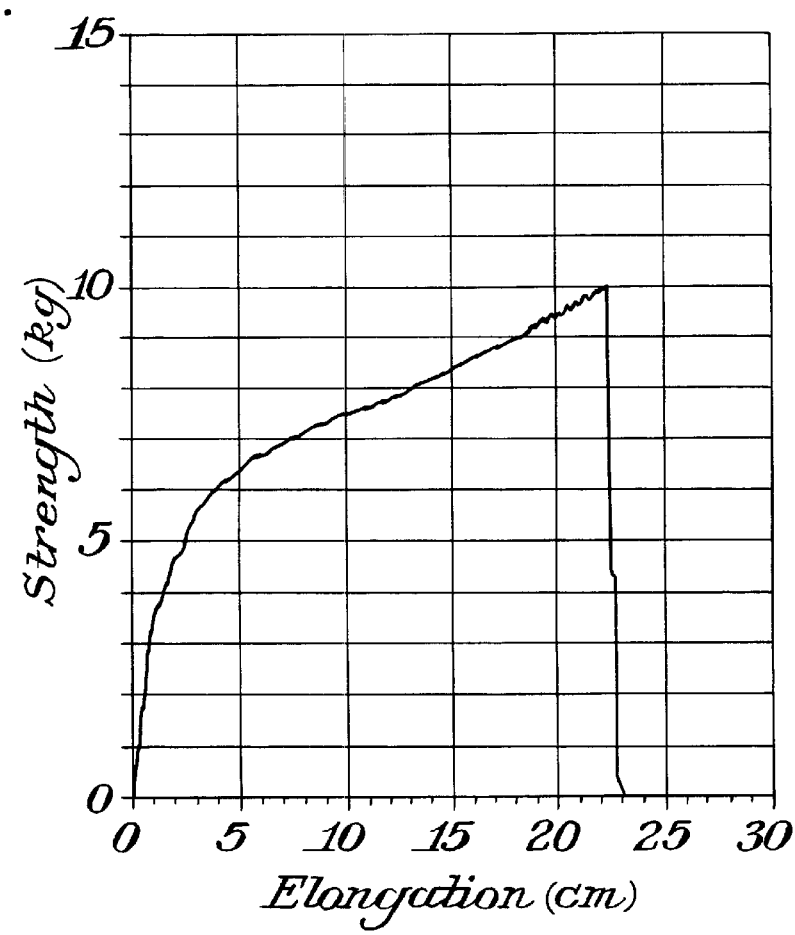

FIG. 1 illustrates a tube 10 made from an ionomeric modified poly-ether-ester in accordance with this invention. Tube 10 has characteristics which make it ideally suited for its intended uses as an improved replacement for PVC. For example, using a modification ratio of 3% to 10%, the material will provide seal strengths in excess of 60 psi internal pressure as indicated in Table 1. The material will weld to itself with tensile strengths of 10 kgs for tubes of 5.4 mm outside diameter and a wall thickness of 0.7 mm as indicated in FIG. 4. Such tensile strengths can even exceed 10 kgs.

The welds for tube 10 can be reopened with the same ease as PVC by external finger pressure such as by squeezing.

There is no degradation such as the smoke or particulates characteristic of the PVC with the material of this invention being generated at welding temperatures of 320° C. and exposure times of less than 1. second. The ionomeric modified poly-ether-ester of this invention can be steam or ETO sterilized without geometry changes. In particular the material will permit steam sterilization of itself and the tube contents without changing the sealing or welding conditions because of extremely low water (steam) adsorption or retention.

FIGS. 2, 2A and 2B illustrate use of this invention for urinary drainage application. As shown therein tubing 10 is 5% by weight ionomer modified and is utilized as the tubing which leads from an operative site, such as the patient 12 to a urinary bag 14. Urinary bag 14 may also be made of the ionomeric modified poly-ether-ester of this invention. In use for urinary drainage application the invention has advantages over medical grade (Class VI) di-octyl-phlate (DOP) plasticized PVC. For example, since there is no plasticizer with the material of this invention there is no leaching of plasticizer into the bag solutions as is common with PVC. Additionally, after PVC has leached its DOP, large volumes of PVC particulates are released. This does not happen with the material of this invention.

For urinary drainage application the full bag 14 is to be separated from the patient discharge line so that it can be replaced by a fresh bag. A preferred practice of accomplishing such substitution would be to use the total containment sterile connection device as described in U.S. Pat. Nos. 5,141,592; 5,156,701; 5,158,630; 5,209,800; 5,244,522 and 5,279,685 the details of which are incorporated herein by reference thereto. Such sterile connection device is referred to as TCD®. By using such techniques the discharge line is disconnected at any suitable location such as the location 16. This leaves a portion of the tubing extending from the operative site or patient 12. A new bag 14 is attached by welding a tubing 10 leading from the new bag so that the tube sections become integral at the weld connection at location 16. The full or used bag is completely sealed and set aside to be weighed for total volume and volume per unit time for determining the discharge rate. The sealing is advantageously accomplished because of the sealing characteristics of the ionomeric modified poly-ether-ester. FIG. 2A, for example, shows a seal 18 formed at the top of bag 14 and FIG. 2B shows a seal 20 formed at the discharge line of bag 14 by use of TCD®.

The full bag 14 and its contents can be disposed of as a sealed biological waste. Alternatively, the bag 14 can be suspended on a standard bag holding pole over a commode and the bottom seal 20 can be opened by use of the fingers and thumb as is possible from seals formed by the total containment sterile discharge connection use for PVC. The bag contents will not drain at this point because of lack of air displacement. When the top seal 18 is opened again by finger pressure if desired the bag contents will immediately begin draining. The use of these two seals 18,20 created by the total containment device have the advantage of draining the bag contents without tools and in the manner that the bag contents do not contact the nurse's hands. This feature is of extreme importance to protect the nurses from contamination and also prevents cross-contamination with a hospital ICU facility. Cross-contamination in ICUs is currently a major problem.

The new or empty and sterile bag 14 is welded to the patient line at welding site 16 immediately after removing the full bag to provide uninterrupted flow from the patient.

The following represents an experiment to compare the ionomeric modified poly-ether-ester designated in the experiment as E77-200-7-3 as a substitute for PVC tubing. The E77-200-7-3 was made from a blend of 90% Hytrel poly-ether-ester and 10% Surlyn ionomer. The poly-ether-ester had a hardness of Durometer 30 on the D scale and a melt flow rate of 5 grams/1 minutes. The ionomer had a hardness of Durometer 60 on the D scale and a melt flow rate of 1.3 grams/10 minutes.

Experimental Plan

PART A: (Disconnect Seal Test)
1) Cut the tubing (E77-200-7-3) into 25 samples 6 inches long.
2) Place each sample in the TCDM and perform a disconnect. This will cut the tube sample in half and seal both ends producing 50 sealed pieces of tubing
3) Place each piece of tubing onto the pressure tester and pump up to 60 psi. If the tubing maintains that pressure for 1 minute then it passes.
4) Place the seal of each piece of tubing in the Arbor Press and squeeze the seal 5 times.
5) Remove the tubing from the press and see if the seal has broken open.
6) Repeat steps 4 & 5, 20 times or until the seal breaks, which ever occurs first.
7) Repeat step 3.

PART B: (PVC Disconnect Seal Test)
1) Repeat Part A using 5 samples of PVC tubing.

PART C: (Connect Test)
1) Place two of the disconnect pieces of tubing from PART A into the TCD™ and perform a connect.
2) Record whether the tubing can be popped open or not.
3) Repeat steps 1 & 2 using all 50 pieces, thus producing 25 samples 6 inches long.

PART D: (Welded Flow Test)
1) Using a metal can that has a tubing connector at its base, attach one of the welded 6 inch samples to the can.
2) Fill the can with 2 cups of water and record the amount of time required for the can to drain through the tubing. Make sure that the draining water is caught in another can so that the same amount of water can be used in all the tests.
3) Repeat step 2 with eight more welded tube samples and one non-welded tube sample.

PART E: (Weld Tensile Strength Test)
1) Load and run the Tensile Instrument program "INST-FIXE.BAS". This program wills save to disk the tensile strength curve results for each of the samples, so they can be regenerated using the program "EXCEL".
2) Calibrate the Tensile Instrument.
3) Place one of the welded samples into the clamps of the Tensile instruments and start the test.
4) Stop the test when the lower clamp of the Tensile Instrument reaches the automatic stop switch.
5) Save the results to disk.
6) Repeat the steps 3, 4 & 5 with the remaining 24 samples and one non-welded tubing.

PART F: (Weld Tubing to PVC Tubing)
1) Set the TCD™ to the CONNECT mode.
2) Place one 3 inch piece of Tubing (E77-200-7-3) into one of the TCD™ clamps.
3) Place one 3 inch piece of PVC Tubing into the other TCD™ clamp.
4) Perform the connect operation so that the E77-200-7-3 tubing and the PVC tubing are welded together.
5) Remove the tubing from the TCD™ and record whether the weld can be popped open,
6) Place the E77-200-7-3-PVC tubing in the Tensile instrument and repeat steps 1–5 of PART E.

TABLE 1

Observations and Data:
PART A: (Disconnect Test)

| E77-200-7-3 Tubing | Disconnect Seal Strength of each End | | Seal Squeeze Test using Arbor Press | |
|---|---|---|---|---|
| Sample # | 1st Half of Tubing | 2nd Half of Tubing | 1st Half of Tubing | 2nd Half of Tubing |
| 1 | 61 psi* | 60 psi* | 100 squeezes* | 100 squeezes* |
| 2 | 60 psi* | 60 psi* | 100 squeezes* | 100 squeezes* |
| 3 | 60 psi* | 60 psi* | 100 squeezes* | 100 squeezes* |
| 4 | 60 psi* | 60 psi* | 100 squeezes* | 100 squeezes* |
| 5 | 60 psi* | 60 psi* | 100 squeezes* | 100 squeezes* |
| 6 | 60 psi* | 60 psi* | 100 squeezes* | 100 squeezes* |
| 7 | 60 psi* | 60 psi* | 100 squeezes* | 100 squeezes* |
| 8 | 62 psi* | 60 psi* | 100 squeezes* | 100 squeezes* |

TABLE 1-continued

Observations and Data:
PART A: (Disconnect Test)

| E77-200-7-3 Tubing | Disconnect Seal Strength of each End | | Seal Squeeze Test using Arbor Press | |
|---|---|---|---|---|
| Sample # | 1st Half of Tubing | 2nd Half of Tubing | 1st Half of Tubing | 2nd Half of Tubing |
| 9 | 62 psi* | 61 psi* | 100 squeezes* | 100 squeezes* |
| 10 | 60 psi* | 60 psi* | 100 squeezes* | 100 squeezes* |
| 11 | 60 psi* | 60 psi* | 100 squeezes* | 100 squeezes* |
| 12 | 60 psi* | 60 psi* | 100 squeezes* | 100 squeezes* |
| 13 | 60 psi* | 60 psi* | 100 squeezes* | 100 squeezes* |
| 14 | 60 psi* | 60 psi* | 100 squeezes* | 100 squeezes* |
| 15 | 60 psi* | 64 psi* | 100 squeezes* | 100 squeezes* |
| 16 | 60 psi* | 60 psi* | 100 squeezes* | 100 squeezes* |
| 17 | 60 psi* | 60 psi* | 100 squeezes* | 100 squeezes* |
| 18 | 60 psi* | 60 psi* | 100 squeezes* | 25 squeezes |
| 19 | 60 psi* | 61 psi* | 100 squeezes* | 100 squeezes* |
| 20 | 60 psi* | 60 psi* | 100 squeezes* | 100 squeezes* |
| 21 | 62 psi* | 60 psi* | 100 squeezes* | 100 squeezes* |
| 22 | 60 psi* | 60 psi* | 100 squeezes* | 100 squeezes* |
| 23 | 60 psi* | 63 psi* | 100 squeezes* | 100 squeezes* |
| 24 | 60 psi* | 60 psi* | 100 squeezes* | 100 squeezes* |
| 25 | 61 psi* | 60 psi* | 100 squeezes* | 100 squeezes* |

Note:
*indicates the seal did not break or leak.

TABLE 2

PART B: (PVC Disconnect Test)

| PVC Tubing | Disconnect Seal Strength of each End | | Seal Squeeze Test using Arbor Press | |
|---|---|---|---|---|
| Sample # | 1st Half of Tubing | 2nd Half of Tubing | 1st Half of Tubing | 2nd Half of Tubing |
| 1 | 62 psi* | 60 psi* | 10 squeezes | 10 squeezes |
| 2 | 60 psi* | 60 psi* | 15 squeezes | 10 squeezes |
| 3 | 60 psi* | 60 psi* | 10 squeezes | 15 squeezes |
| 4 | 62 psi* | 63 psi* | 10 squeezes | 10 squeezes |
| 5 | 60 psi* | 60 psi* | 20 squeezes | 10 squeezes |
| 6 | 60 psi* | 60 psi* | 10 squeezes | 10 squeezes |
| 7 | 60 psi* | 60 psi* | 10 squeezes | 15 squeezes |
| 8 | 62 psi* | 60 psi* | 5 squeezes | 10 squeezes |
| 9 | 60 psi* | 63 psi* | 10 squeezes | 10 squeezes |
| 10 | 60 psi* | 60 psi* | 10 squeezes | 10 squeezes |

Note:
*indicates the seal did not break or leak.

PART C: (Ability of Weld to Pop Open)

All 25 connected (welded) Samples (E77-200-7-3) popped open easily

TABLE 3

PART D: (Effect of Weld on Water Flow through E77-200-7-3 Tubing)

| Sample # | Flow Time (sec) | Flow Time (sec) | Flow Time (sec) | Avg. Flow Time (sec) | Flow Change (%) |
|---|---|---|---|---|---|
| No Weld | 90.74 | 90.41 | 90.3 | 90.48 | 100% |
| 1 | 97.97 | 98.29 | 98.4 | 98.22 | 91.40% |
| 2 | 101.27 | 101.6 | 100.9 | 101.25 | 88.10% |
| 3 | 95.88 | 95.21 | 95.28 | 95.45 | 94.50% |
| 4 | 93.51 | 92.89 | 93.45 | 93.28 | 96.90% |
| 5 | 104.45 | 103.52 | 103.44 | 103.81 | 85.20% |
| 6 | 101.24 | 100.96 | 100.26 | 100.82 | 88.60% |
| 7 | 101.62 | 100.34 | 100.12 | 100.69 | 88.70% |
| 8 | 98.67 | 97.81 | 97.27 | 97.91 | 91.80% |
| 9 | 99.64 | 99.65 | 99.48 | 99.59 | 89.90% |

An advantage of the ionomeric modified poly-ether-ester is its ability to be effectively welded to conventional PVC. This is important because it permits the replacement of some of the PVC components with the new material. Thus, for example, in CAPD usage it is necessary to remove a used filled bag for replacement by a new empty bag. The conventional PVC tubing could be cut and tubing from the new material could be welded to the remaining PVC tube segment. The new material components could thus gradually replace their PVC counterparts. FIG. 3 demonstrates the weld strength of PVC tubing to ionomeric modified poly-ether-ester tubing.

FIGS. 3 and 4 are graphs illustrating the ability of the weld to pop open. As shown therein with use of the ionomeric modified poly-ether-ester of this invention (FIG. 4) the unsealing characteristic is accomplished with approximately the same ease as in PVC tubing welded to the modified poly-ether-ester tubing (FIG. 3).

Figure 5:
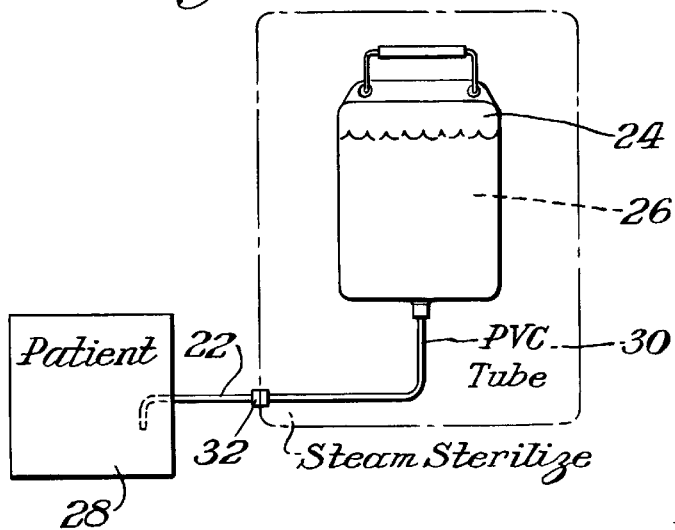
FIG. 5 is a schematic view of a prior art system for steam sterilizing when using PVC tubing in peritoneal dialysis.
Figure 6:
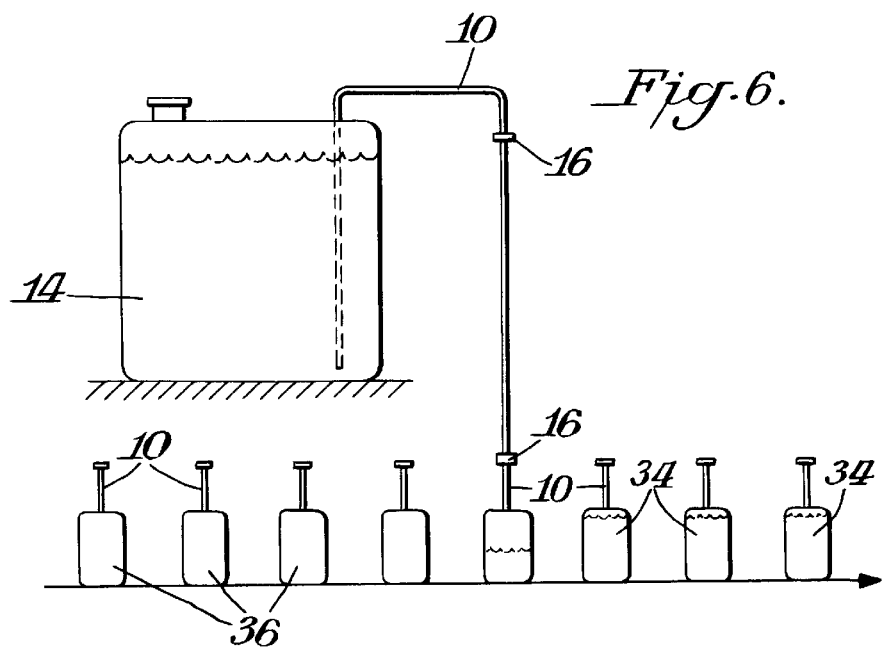
FIG. 6 is a schematic view showing a sterile solution fed to sterile bags using the ionomeric modified poly-ether-ester of this invention.

FIGS. 5–6 illustrate use of the invention with respect to peritoneal dialysis (CAPD). FIG. 5 represents the prior art practices wherein a tube 22 is utilized made from PVC. In such applications PVC is the material of choice of the health care industry for both the tubing and the solution bags 24. The reasons for favoring PVC are that its long standing use started early in the 1960s. Additionally, there is film clarity for visual clarification and PVC provides low cost and abundant supplies. The PVC used for peritoneal dialysis, however, must undergo bulk sterilization after packaging to insure sterility to the entire product offering prior to patient use. Steam sterilization (250° F. for thirty minutes) of PVC in contact with dialysis solutions causes several serious problems. For example, the PVC plasticizer (DI-OCTYL-PHLATE), DOP, leaches out of the PVC composition during steam sterilization and into the dialysis solution. DOP is under suspicion of being a low level carcinogen. A further product that is after DOP leaching the residual PVC composition is vulnerable to particulates being formed and entering the dialysis solution which in turn enters the patient's body. Further, water adsorption (from the steam sterilization) into the patient tubing and bags reduces the plastic strength by approximately 50% causing bag leakage and sterility failures. FIG. 5 illustrates the conventional practice of using PVC as a material for the tubing 22 and bag 24 wherein the solution 26 in the bag 24 is caused to flow through tubing 22 to the patient's site 28. Steam sterilization takes place in chamber 30. FIG. 5 also illustrates the separation and connection area 32 used for replacing solution bags by separating and then rejoining the PVC transfusion line 22.

FIG. 6 illustrates use of the ionomeric modified poly-ether-ester for the tube 10 and bag 14. This material overcomes the PVC problems in several ways without sacrificing the positive attributes of PVC. With the material of this invention there is no plasticizer, thus leaching is not a problem. The material also does not form particulates and is impervious to steam sterilization to retain 100% of its strength. The ionomeric modified poly-ether-ester has another positive feature that is unique to sterile connection devices that use a heated blade to achieve sterility. The material does not make smoke. Conversely, when PVC is heated using the TCD™ instrument of the aforenoted patent the plasticizer DOP evolves as fine aerosol droplets that gives the appearance of smoke. Means must be provided therefore to contain and dispose of the smoke harmlessly. Since the poly-ether-ester of this invention has no plasticizer, no smoke is formed using the TCD™ process.

The use of the total containment device TCD™ has a more significant potential for peritoneal dialysis, however, in that steam sterilization and its problems can be avoided entirely. For example, the ionomeric modified poly-ether-ester consumable bags, tubes, etc. can be bulk sterilized by ethylene oxide at the point of manufacture. The solutions can also be sterilized in bulk storage tanks and made ready to fill the previously sterilized bags. Using the TCD™ the sterile solutions can be fed to the sterile consumable thus avoiding steam sterilization. FIG. 6 illustrates by use of the connect/disconnect areas 16 how the ionomeric modified poly-ether-ester of this invention for tubing 10 can be used for replacing bags thereby resulting in a plurality of filled bags 34 with the unfilled bags 36 ready to be connected by weld 16 which would join its tubing 10 to the tubing leading from the sterile solution container 14.

Figure 7:
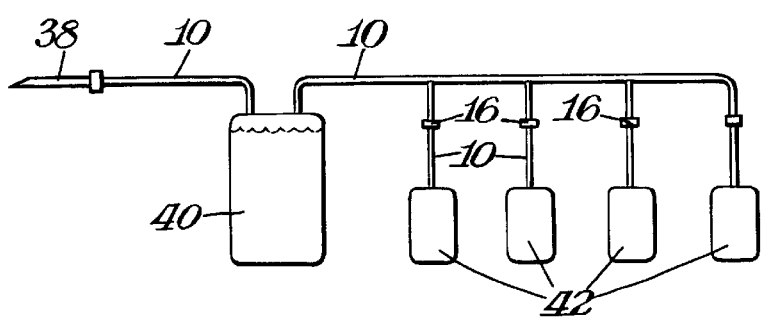
FIG. 7 is a schematic view showing a primary blood bag and four satellite bags connected by the tubing of this invention as used. in blood processing.

FIG. 7 illustrates use of the invention for blood processing. In this application the use of ionomeric modified poly-ether-ester materials has several end-use advantages. Since the material has no plasticizers the problems of plasticizer leaching into the blood are eliminated. The problems of mixing and matching of various sources of blood bags and tubing are also eliminated. Mixing and matching is viewed by the FDA as a health threat when bags and tubing of unknown source and composition are introduced into blood centers because of cost or availability. Eventually the material can be frozen and retain its flexibility, thus avoiding brittle fracture.

Mix and match is considered by the FDA as a serious quality control and safety problem in the blood processing industry. Mix and match is an expression used to describe the chaotic situation in blood banks brought on by economics. Blood banks buy blood bags and tubing strictly on price without too much regard to source. Global dumping practices, questionable polymer compositions and tube size variation all contribute to the problem. In order. to exercise a measure of control the FDA would prefer to be able to mandate a set of regulations regarding tube quality and be able somehow to exclude tubing that does not meet the FDA criteria.

The ionomeric modified poly-ether-ester material meets this requirement again because the material does not contain plasticizers. Commonly used medical grade PVC contains up to 40% by weight DOP as a plasticizer that vaporizes to a smoke when the welding temperature exceeds 200° C. By using what amounts to a small smoke detector in the TCD™ the instrument can detect the smoke generation and refuse to complete the welding cycle. specifically, prior to making a weld the tube ends are made to touch the wafer for one second. If no smoke is generated the process will proceed to make a weld. If smoke is detected the instrument will abort. In this way, the mixture will mix and match problem so important to the FDA and safety of the nation's blood supply can be avoided.

Use of the ionomeric modified poly-ether-esters have a positive effect when used in conjunction with TCD™ in that tube sealing (separating) can be accomplished in the TCD as well as connections. Blood banks have the capability of sealing off tubing by radio frequencies (RF) sealers. Because of the radio frequency, however, the equipment is normally located away from the blood processing areas and shielded for safety (booths). The inconvenience of going to a sealer encourages people to make poor seals via hot plates and bunsen flames rather than taking the bags to the RF sealer. Use of the TCD™ avoids this problem. The TCD™ is located in the work place. The use of the TCD™ in blood banking has another important advantage. It is called "unbundling" and means complete flexibility to disconnect and connect blood bags at will. Without the sterile connection technology afforded by TCD™ this concept is not possible. For example, when blood is collected at the blood banks it is not known at that time what blood fractions will be required to meet end use needs. To overcome this unknown all blood is collected in bag sets. That is, a primary blood bag and four satellite bags are sent as a sterilized set. This is illustrated in FIG. 7 wherein the blood supply needle 38 has its tubing 10 leading to primary blood bag 40 with tubing 10 also leading to the four satellite bags 42 each of which has its tubing 10 connected to the main tubing by the TCD™ connect or disconnect location 16.

After the blood is centrifuged the fractions are expressed over into various component bags and sealed off. Once sealed off the bags can not be re-entered without compromising sterility. In the practice of this invention all of the tubing 10 and the various bags 40,42 would be made of the ionomeric modified poly-ether-ester material.

If, for example, only whole blood is needed, the four unused satellite bags 42 are separated and discarded. At approximately $2.00 per bag this loss is keenly felt by the blood bank. Moreover, if the bags are used and sealed it is not possible to enter the bags to enhance the cell life by the addition of stabilizers, nutrients or enhancers without compromising sterility.

The use of the TCD™ has made "un-bundling" possible. The TCD™ is designed to sterilely disconnect and connect sterile containers at will thereby providing the medical profession a desired level of flexibility and at lower consumable costs.

The use of the ionomeric modified poly-ether-ester materials has proven to be non-pyrogenic to human tissue through wide spread use of permanently placed interval sutures. For this reason, the poly-ether-ester material is approved by the FDA for internal human use and is ideal for blood bags.

Figure 8:
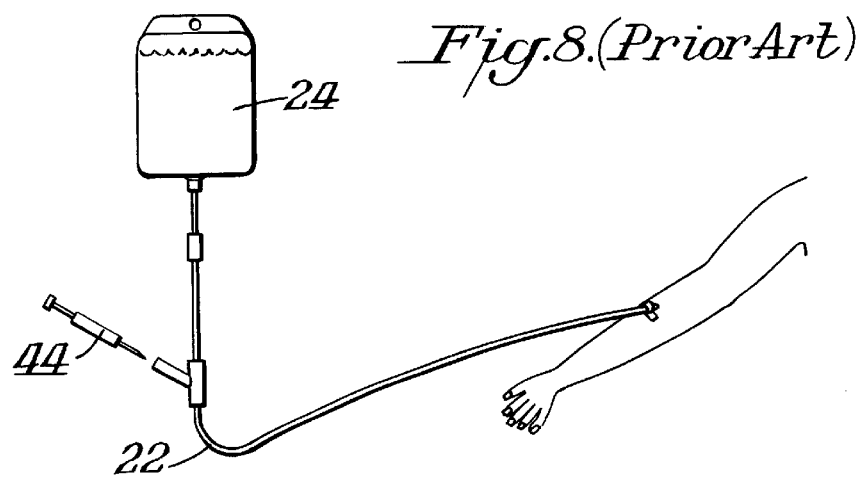
FIG. 8 is a schematic view showing prior art chemotherapy treatment using PVC tubing.
Figure 9:
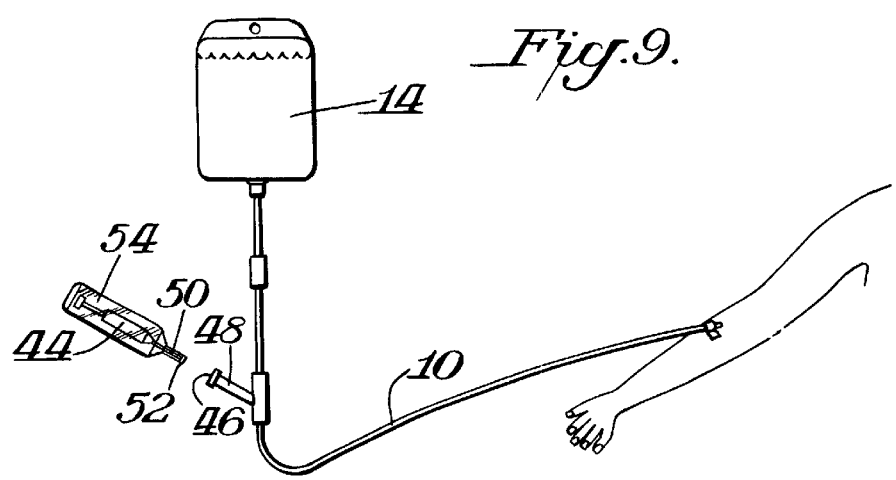
FIG. 9 is a view similar to FIG. 8 showing use of the tubing of this invention.

FIGS. 8–9 relate to use of the invention for chemotherapy. FIG. 8 illustrates the conventional practice to administer chemo-therapeutic drugs for cancer patients by introducing the drugs via syringe 44 or a pump into the intra-venous transfer tubing 22. Solution would also flow into PVC tubing 22 from PVC bag 24. The syringe port is a convenient entry site for bacteria. For patients whose immune system is depressed from the therapy bacteria entry is life threatening. This problem can be eliminated by the use of the TCD™ instrument.

Use of the TCD™ instrument in combination with the ionomeric modified poly-ether-ester material for chemotherapy application has several end use advantages. Since there is no plasticizers involved, the danger of plasticizer leaching into the patient is eliminated. Since there are no particulates this form of contamination into the patient's blood stream is also eliminated. The poly-ether-esters are already used widely within humans for sutures and arterial repair. They present no pyro-genic defects therefore for human use.

FIG. 9 illustrates use of ionomeric modified poly-etherester material for bag 14 and tubing 10. As shown therein at the normal entry port location 46 a ionomeric modified poly-ether ester tube 48 is spliced into the line 50 also made of ionomeric modified poly-ether-ester and is terminated with a closed (sealed) distal end 52. The syringe 44 or pump is sterilely enclosed in a sheath 54 and terminated with a closed sealed distal end.

Making a sterile connection via the TCD™ the connection is totally contained. No bio-burden can enter the patient and no chemotherapy agents can escape outside the system. The syringe can also be sterilely disconnected by the TCD™ when the procedure is complete.

Figure 10:
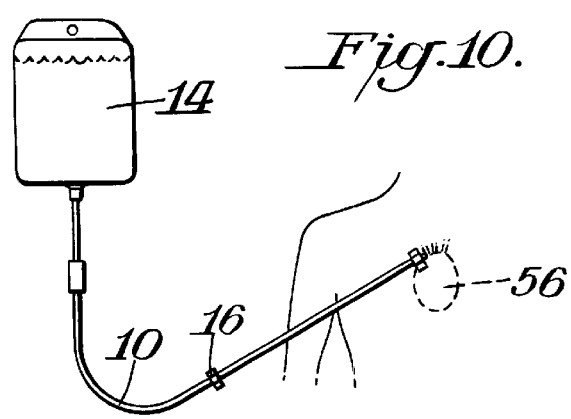
FIG. 10 is a schematic view showing parenteral feeding of the body using the tubing of this invention.

FIG. 10 illustrates use of the invention for parenteral feeding. For cancer patients who have suffered alimentary tract removal because of the cancer, feeding is accomplished by liquid nutrients fed into the patient's blood stream by way of a tube inserted into a sub-clavian vein and then into the heart.

Long term implantation of PVC tubing is also a problem. PVC plasticizer extraction directly into a patient's blood stream is particularly troublesome.

As pointed out in *Biocompatible Polymers, Metals and Composites* by M. Szycher, Sponsored by Society of Plastics Engineers Inc., Techmonic Publishing Co. 1983, flexible PVC compounds can contain up to 40% plasticizer. While the chosen material is very carefully selected for its high purity and low toxicity, it can be extracted from PVC by contact with some fatty substances, such as by blood or the digestive system. When contact times are short there is no difficulty, but for a number of applications in which PVC may be in contact with the patient's system for longer periods extraction of plasticizer is much less acceptable. Stiffening of PVC due to plasticizer being extracted may cause patient's considerable discomfort when a feeding or wound drainage tube is removed after prolonged use. Blood stored in PVC bags or flowing through PVC tubes for long periods will also extract plasticizer. While that most commonly used, DEHP, has been shown to be of low toxicity it is naturally desirable to avoid any extra burden on a patient's system. This is obviously more important for those needing regular hemodialysis for blood transfusions.

The use of ionomeric modified poly-ether-ester materials for tubing is beneficial in two ways. There is no leaching of plasticizers into the patient's system from the implanted tube. Additionally, the poly-ether-ester material is compatible with the TCD™ for making sterile connects and disconnects from the implant. FIG. 10, for example, illustrates the use of a poly-ether-ester bag 14 supplying the liquid nutrients through poly-ether-ester tubing 10 into the patient's heart 56. By use of the TCD™ a sterile connect/disconnect procedure 16 can be effectively used to replace the bag 14 with a new bag 14.

The invention may also be used for cell culturing and particularly has applications in connection with the TCD™ in biotechnology. In such applications the ionomeric modified poly-ether-ester would be used as tubing from the reactor.

Biotechnology is a rapidly growing business area with R&D expenditures of $2 BLN in 1994 (U.S.). TCD™ technology can fill unmet needs for improved connections in several segments of this market. The value-in-use is a $2–10/ connection with a total market opportunity of $28 MM (1990) and estimated to grow to $78 MM (1995). Mammalian cell fermentation is targeted as the market entry segment for the TCD™ technology.

The biotechnology business utilizes many techniques developed by molecular and cellular biologists in the 1980's for increasing the production of a specific protein in a cell by redesigning, or engineering, its DNA. This business area produced high value proteins which are used in diagnosis or therapy of diseases as well as cost reducing processes in energy conversion and agriculture processes. The common factors in all biotechnology segments are the creation and isolation of a unique cell type and then the growth of this cell to isolate product(s).

Cell growth occurs in a sterilely isolated system which provides nutrients and removes waste products, a process called fermentation. To maximize product yield, this fermentation system must also prevent the entry of other "non-unique" cells which would grow and contaminate the system.

The technology to produce and isolate unique cells is well developed, although it requires highly skilled personnel. Unique cells may be created from either bacteria or cells isolated from more complex organisms, including humans. The technology to grow large quantities of bacterial cells is well established. Cells from complex organisms, called mammalian cells, grow more slowly than bacterial cells and require more complex nutrients. the development of new ways to grow these unique mammalian cells in large quantities is one of the major problems in biotechnology today.

Preventing non-unique cells from entering the fermentation system is important for all types of cells. In bacterial systems contamination is not as significant because of the design of fermentors and the length of the fermentation process, a few days. A typical mammalian cell fermentation cycle is three weeks long but the nutrients and wastes are exchanged several times a day. Accidentally introducing bacterial contamination when exchanging the fluids is a real possibility. Such contamination destroys the mammalian cells in several days.

Presently about 90% of the products produced by biotechnology are grown in bacterial cells lines. However, research is focusing more on producing unique cells from mammalian cells because some proteins can be produced more effectively in these cells. By 1995, it is expected that at least 50%, and perhaps as much as 90%, of the genetically engineered products for health care will be produced from mammalian cells.

The biotechnology market may be segmented in several different ways, the preferred methods are by product source and by stage of the product development cycle. Product source defines the type of cell the protein is isolated from and product development cycle defines whether the product is in the stage of research, development, or manufacturing. The following charts give more information on segmentation and estimates of value-in-use (VIU) and market opportunity for the TCD™ technology. To date, market analysis has been focused on th e high value products for health care applications. The segmentation and rest of this discussion focuses on th is area.

The early phase of product development, research, is done by a large number of highly skilled scientists whose primary objective is the construction and isolation of unique cells with specific properties. Cell growth in research is done on a small scale and lose due to contaminations of a fermentation, although a nuisance, has small economic consequences. However, in the development and manufacturing phases, where the objective is the growth of large quantities of these unique cells, contamination results in a significant economic loss.

The following tables compare several important aspects of the termination process and the market opportunity by cell type.

| Cell Type | Average Length of Fermentation Cycle | Number of Connections Per Cycle | Relative Value of Materials | Average VIU Per Connection |
| --- | --- | --- | --- | --- |
| Bacterial | 4 Days | 8 | 1X | $3 |
| Mammalian | 21 Days | 60 | 10X | $7 |
| Whole Organ | 21 Days | 42 | 8X | $4 |

| Cell Type | Number of Connections | | Market Opportunity | |
| --- | --- | --- | --- | --- |
| | 1994 | 2000 | 1994 | 2000 |
| Bacterial | 5.2 MM | 7.9 MM | $11 MM | $17 MM |
| Mammalian | 3.0 MM | 8.5 MM | $15 MM | $58 MM |
| Whole Organ | 0.5 MM | 0.8 MM | $2 MM | $3 MM |
| TOTAL | 8.7 MM | 17.2 MM | $28 MM | $78 MM |

The increase in the number of products in the development and manufacturing phases as well as more products derived from mammalian cells, both with higher VIU's, account for much of the growth in the market opportunity.

The initial targets for the TCD™ are the development and manufacturing phases of mammalian cell culture. The reasons for this choice are:

significant product loss due to contamination
high VIU per connection
very high income potential per TCD™ placement
rapidly growing segments
technology still evolving.

Our initial TCD™ placements will be with small companies which produce monoclonal antibodies by mammalian cell culture on contract to other companies. These antibodies are used in diagnostic tests and are in clinical studies for disease treatments.

Six companies worldwide produce monoclonals on contract which sell for $2 M to $5 M per gram. Their 1990 sales were $3 MM and are forecast to grow to $8 MM (1995) and as high as $60 MM (2000). The demand for monoclonal products exceeds the present capacity of these companies. In addition, at least 20 companies produce monoclonals for their own use. At contract companies, the product loss due to fermentation system contamination is approximately 15%/week. Discussions with these companies indicate that most of this contamination appears to occur when entering the system to add fresh nutrients and remove wastes and product (the monoclonals produced by the cells). Presently, there is no simply means to sterilely access these fermentation systems.

The strategies for market development in the U.S. are:
establish the TCD™ as the state-of-the-art connection technology;
utilize scientific meetings and seminars to expose TCD™ technology to marketplace;
initially place the TCD™ in a high value-in-use segment.

Establishing the TCD™ as the standard connection technology for biotechnology depends on demonstrating its effectiveness in reducing contamination. Its convenience and simplicity will also be important. Effectively demonstrating these attributes requires information collected under normal use conditions.

Developing and publishing the experience of TCD™ in cell culture will create the exposure to develop a demand for this technology in the other biotechnology applications and help establish the TCD™ as the state-of-the-art connection technology for this market.

In addition to the above described uses of the invention the ionomeric modified poly-ether-ester may also be used in food processing particularly as tubing for fluids and semi-solids and as the material for making sheets and films for bacterial and virus extrusion. When used as sheets or films, the sheet could be draped over the patient and the surgeon would cut through the sheet into the patient. The ionomeric modified poly-ether-ester may in effect be used as a suitable replacement for PVC in virtually all uses of PVC.

While the invention has been particularly described with respect to a composition which consists essentially of an ionomeric modified poly-ether-ester the invention may be modified to include minor amounts of PVC, such as disclosed in co-pending application Ser. No. 742,046, filed Nov. 1, 1996, the details of which are incorporated herein by reference thereto. In addition, the material could be modified to include minor amounts of silica, particularly silicon oil in an amount of 5–10% by weight of the final composition or colloidal silicon dioxide in an amount of 1% to 3% by weight of the final composition. Such addition of a minor amount of silica could be incorporated into the composition either alone or in addition to the minor amount of PVC.

What is claimed is:

1. A container for use in an assembly adapted for transferring a medical fluid from a first location to a remote second location wherein the fluid would be in a container at one of the locations and the fluid would be conveyed through tubing communicating with the container, the improvement being in that said container is made from a composition consisting essentially of an ionomeric modified poly-ether-ester material containing from 1% to 50% by weight ionomer, said poly-ether-ester being a block copolymer containing both polyether and ester blocks modified by an ionomer, said ionomer being a copolymer of ethylene with 1–10% by weight methacrylic acid converted to methacrylate salt, said polyether-ester and said ionomer both individually and in combination being plasticizer-free, said ionomeric modified poly-ether-ester container being steam sterilizable, said ionomeric modified poly-ether-ester material being thermally weldable to itself and to polyvinylchloride, and said container having structure for communicating with the tubing.

2. The container of claim 1 wherein said container is generally transparent and made from a single layer of material.

3. The container of claim 1 wherein said poly-ether-ester and said ionomer have generally the same melting temperature to facilitate their mixing in the making of said container.

4. The container of claim 1, in combination therewith, an assembly for transferring a medical fluid from a first location to a second location, said assembly including tubing whereby the fluid would be in said container at one of said locations and the fluid would be conveyed through said tubing communicating with said container.

5. The assembly of claim 4 wherein said tubing is made from a composition consisting essentially of an ionomeric modified poly-ether-ester material containing from 2% to 15% by weight ionomer, said poly-ether-ester being a block copolymer containing both poly-ether and ester blocks modified by an ionomer, said ionomer being a copolymer of ethylene with 1–10% by weight methacrylic acid converted to methacrylate salt, said poly-ether-ester and said ionomer both individually and in combination being plasticizer-free, said tubing being capable of being welded to itself to form a seal which resist opening at internal pressure up to 60 psi, and said seal being capable of being opened under external finger pressure.

6. The assembly of claim 5 wherein said assembly is a peritoneal dialysis assembly, and said container being a dialysate container for being mounted at a location remote from the patient whereby said tubing may permit flow of fluid between said container and the patient.

7. The assembly of claim 5 wherein said assembly is a urinary drainage assembly, and said container being a urinary container for being remote from the patient whereby said tubing may convey urine from the patient to said container.

8. The assembly of claim 5 wherein said assembly is a blood processing assembly, said blood processing assembly including a blood supply needle and a blood collecting container, container being said blood collecting container, and said tubing being in flow communication with said needle and said blood collecting container.

9. The assembly of claim 5 wherein said assembly is a chemotherapy assembly, said container being a solution container, said tubing leading to a patient to deliver the solution from said container to the patient, and a drug introducing assembly communicating with said tubing to introduce a drug into the solution.

10. The assembly of claim 5 wherein said assembly is a parenteral feeding assembly including a liquid nutrient container, a tube for insertion into the sub-clavian vein of a patient, and said tubing being in flow communication with said container and said tube.

11. The assembly of claim 5 wherein said poly-ether-ester and said ionomer have generally the same melting temperature to facilitate their mix in the making of said container.

12. The assembly of claim 5 wherein said container is generally transparent and made from a single layer of material.

13. The assembly of claim 5 wherein said ionomeric modified poly-ether-ester tubing is welded to and in flow communication with a further tubing made of said ionomeric modified poly-ether-ester.

14. The assembly of claim 5 wherein said ionomeric modified poly-ether-ester tubing is welded to and in flow communication with a further tubing made of polyvinylchloride.

* * * * *